United States Patent
Li

(10) Patent No.: US 6,168,960 B1
(45) Date of Patent: Jan. 2, 2001

(54) BACKSIDE DEVICE DEPROCESSING OF A FLIP-CHIP MULTI-LAYER INTEGRATED CIRCUIT

(75) Inventor: Xia Li, Fremont, CA (US)

(73) Assignee: Advanced Micro Devices, Inc., Sunnyvale, CA (US)

( * ) Notice: Under 35 U.S.C. 154(b), the term of this patent shall be extended for 0 days.

(21) Appl. No.: 09/126,072

(22) Filed: Jul. 30, 1998

(51) Int. Cl.$^7$ ............................. A01L 21/66; G01R 21/36
(52) U.S. Cl. ............................ 438/14; 438/15; 438/16; 438/17; 438/18; 438/108; 257/778
(58) Field of Search .................................. 438/14, 15, 16, 438/17, 18, 108; 257/778

(56) References Cited

U.S. PATENT DOCUMENTS

| | | | |
|---|---|---|---|
| 5,214,283 | * | 5/1993 | Le . |
| 5,401,972 | * | 3/1995 | Talbot et al. . |
| 5,821,549 | * | 10/1998 | Talbot et al. ........................... 250/307 |
| 5,834,323 | * | 11/1998 | Ghafghaichi et al. ................. 438/17 |
| 5,904,489 | * | 5/1999 | Khosropour et al. . |
| 5,920,765 | * | 7/1999 | Naum et al. . |
| 5,952,247 | * | 9/1999 | Livengood et al. . |
| 5,972,725 | * | 10/1999 | Wollesen et al. . |
| 6,069,079 | * | 5/2000 | Li . |
| 6,093,331 | * | 7/2000 | Wollesen . |

OTHER PUBLICATIONS

Chao et al, "An extration method to determine interconnect parasitic parameters," IEEE Trans. on Semi. Man., /vol. 11, No. 4, pp. 615–623, Nov. 1998.*
Lee, "Electron–Beam Probaing," IEEE Design & Test of Computers, pp. 36–49, 1989.*

* cited by examiner

Primary Examiner—John F. Niebling
Assistant Examiner—Jonathan Hack
(74) Attorney, Agent, or Firm—Sawyer Law Group LLP

(57) ABSTRACT

Aspects for deprocessing of a flip-chip, multi-layer integrated circuit from the backside are described. In an exemplary method aspect, the method includes reducing a first backside layer of the multi-layer integrated circuit to a predetermined thickness, and exposing an active region of the multi-layer integrated circuit to allow device analysis of the multi-layer integrated circuit. The method further includes removing a metal layer beneath the active region to expose interlayer dielectric material, performing a bulk delayering of the interlayer dielectric material to expose a next metal layer, and continuing to delayer the multi-layer integrated circuit layer-by-layer from the backside for analysis of the multi-layer integrated circuit.

9 Claims, 4 Drawing Sheets

BACKSIDE DEVICE DEPROCESSING OF A FLIP-CHIP MULTI-LAYER INTEGRATED CIRCUIT

FIELD OF THE INVENTION

The present invention relates to multi-layer integrated circuit (IC) devices, and more particularly to device deprocessing for analysis of a multi-layer integrated circuit device from a backside of the device.

BACKGROUND OF THE INVENTION

For flip-chip, multi-layer IC devices, debugging for physical defects in the IC is difficult due to having to approach the desired layers from the backside of the device. FIG. 1 illustrates a sideview of a portion of a typical flip-chip configuration. As shown in FIG. 1, an IC device 10 is coupled to a ceramic package 12 (e.g., a C4 package) via solder bump 14. The solder bump 14 acts as a chip-to-carrier interconnect to attach the IC device 10 to the ceramic package 12 and to mate with corresponding pad patterns to form the necessary electrical contacts between the circuit(s) of the IC device 10 and pins of the package 12. To analyze the IC device 10, the thick silicon substrate 16, e.g., on the order of 530 microns ($\mu$m) thick, which is the top layer seen from the backside of the IC device 10, must be reduced.

A common approach to reduce the silicon thickness is to utilize mechanical polishing of the device. The mechanical polishing used from the backside removes the silicon and creates a very thin device. The reduced thickness allows utilization of an infrared (IR) optical device to view the device. Unfortunately, the thin device created by polishing is difficult to handle and subsequently utilize in further device analysis, which normally requires the removal of the device from the package to perform well-established delayering techniques from a frontside of the device. Breakage of the device often occurs due to the thinness of the device and brittleness of the silicon. Thus, the process is highly problematic and significantly time-consuming.

Accordingly, a need exists for efficient device analysis from the backside for flip-chip IC devices. The present invention addresses such a need.

SUMMARY OF THE INVENTION

The present invention provides for device deprocessing from the backside in flip-chip multi-layer integrated circuits. In an exemplary method aspect, the method includes reducing a first backside layer of the multi-layer integrated circuit to a predetermined thickness, and exposing an active region of the multi-layer integrated circuit to allow device analysis of the multi-layer integrated circuit. The method further includes removing a metal layer beneath the active region to expose interlayer dielectric material, performing a bulk delayering of the interlayer dielectric material to expose a next metal layer, and continuing to delayer the multi-layer integrated circuit layer-by-layer from the backside for analysis of the multi-layer integrated circuit.

Through the present invention, more efficient device analysis is achieved for flip-chip devices. The present invention achieves effective delayering from the backside, thus avoiding problems associated with device removal for frontside delayering. These and other advantages of the aspects of the present invention will be more fully understood in conjunction with the following detailed description and accompanying drawings.

DETAILED DESCRIPTION

The present invention relates to device deprocessing from a backside in multi-layer integrated circuit flip-chip devices. The following description is presented to enable one of ordinary skill in the art to make and use the invention and is provided in the context of a patent application and its requirements. Various modifications to the preferred embodiment and the generic principles and features described herein will be readily apparent to those skilled in the art.

For illustrative purposes, device deprocessing, i.e., device analysis and delayering, in accordance with the present invention is described with reference to an overall flow diagram of processing steps shown in FIG. 2 in conjunction with FIGS. 3, 4, 5, 6, and 7 which illustrate partial cross-sectional views of a flip-chip, multi-layer integrated circuit during the steps of the processing.

Figure 1:
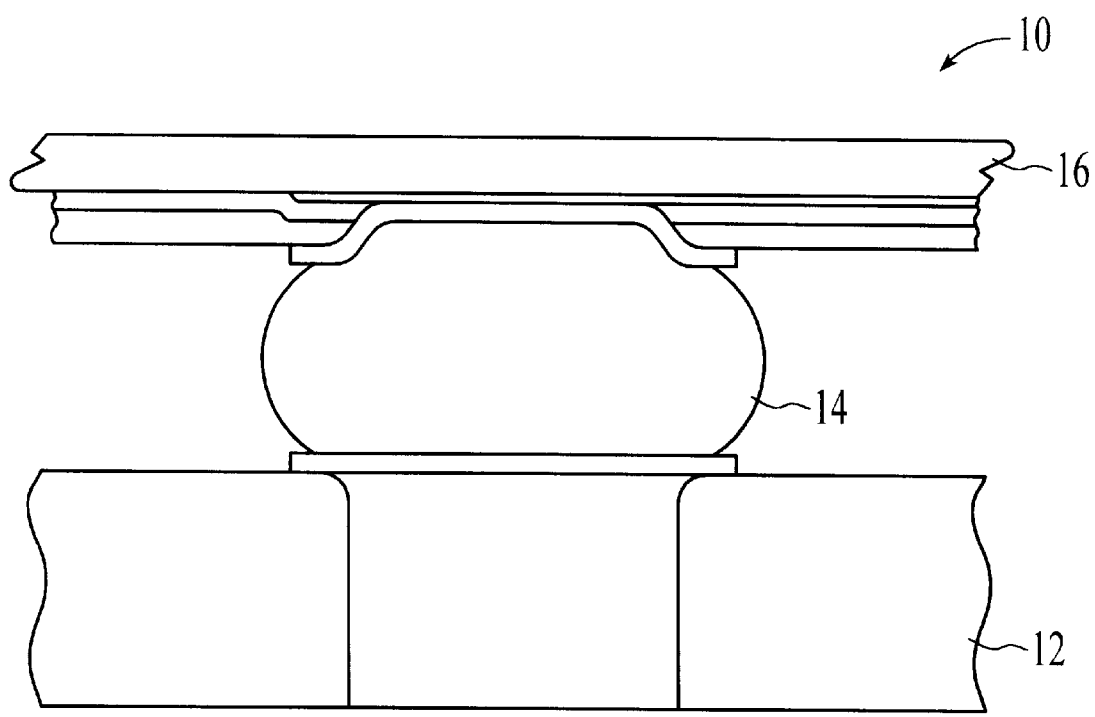
FIG. 1 illustrates a representation of a sideview of a typical flip-chip multi-layer integrated circuit.
Figure 2:
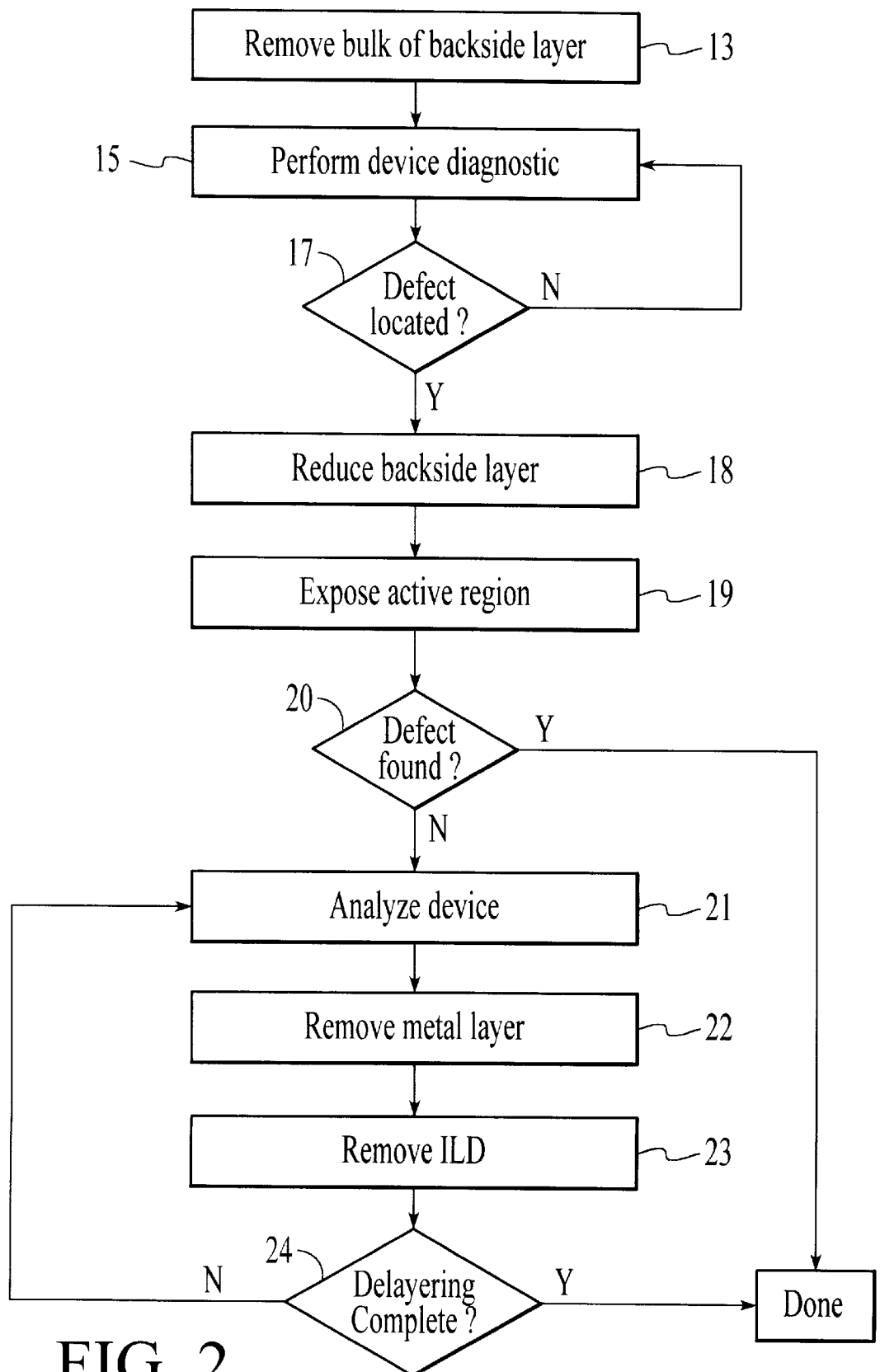
FIG. 2 illustrates a flow diagram of device deprocessing from a backside of a flip-chip IC in accordance with the present invention.

FIG. 2 illustrates a block flow diagram of a process for device deprocessing from a backside for flip-chip, multi-layer IC devices. To prepare for deprocessing of a device, initially a bulk amount of a backside layer, e.g., silicon, is removed (step 13). Suitably, the thickness is reduced from about 530 $\mu$m to about 100 $\mu$m through mechanical polishing or RIE (reactive ion etching) for silicon, as is well appreciated by those skilled in the art. Device diagnostics are then performed (step 15) using standard diagnostic routines, such as examination with an emission microscope. The diagnostic routine is preferably continued until an area with a defect is located, as determined via step 17. Once a defect is located, device deprocessing commences.

Figure 3:
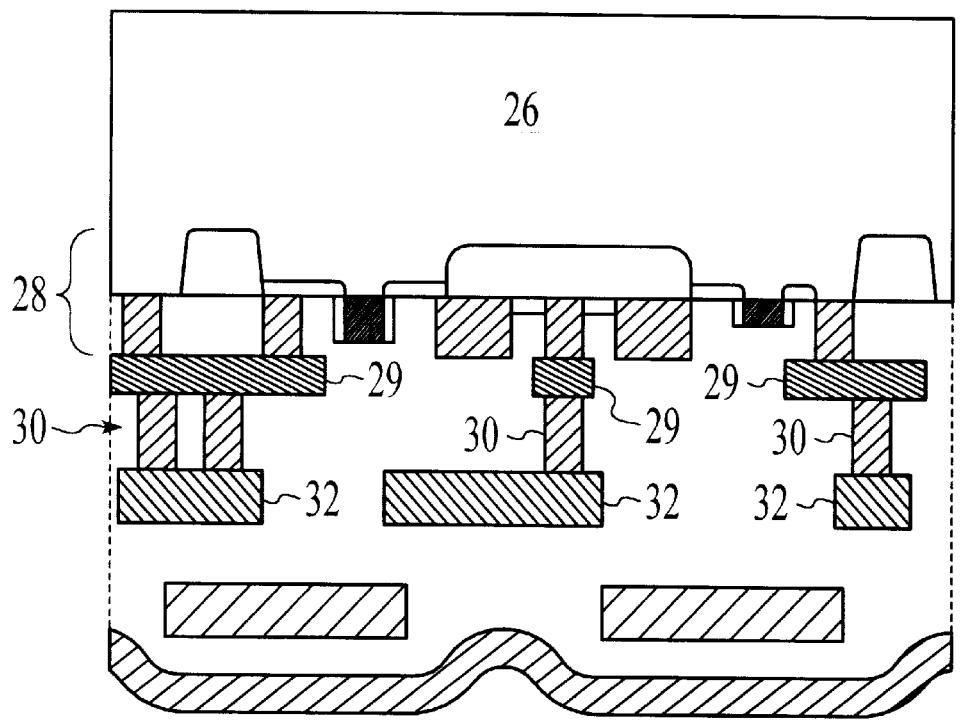
FIG. 3 illustrates a partial cross-section of a flip-chip device to be deprocessed according to the present invention.
Figure 4:
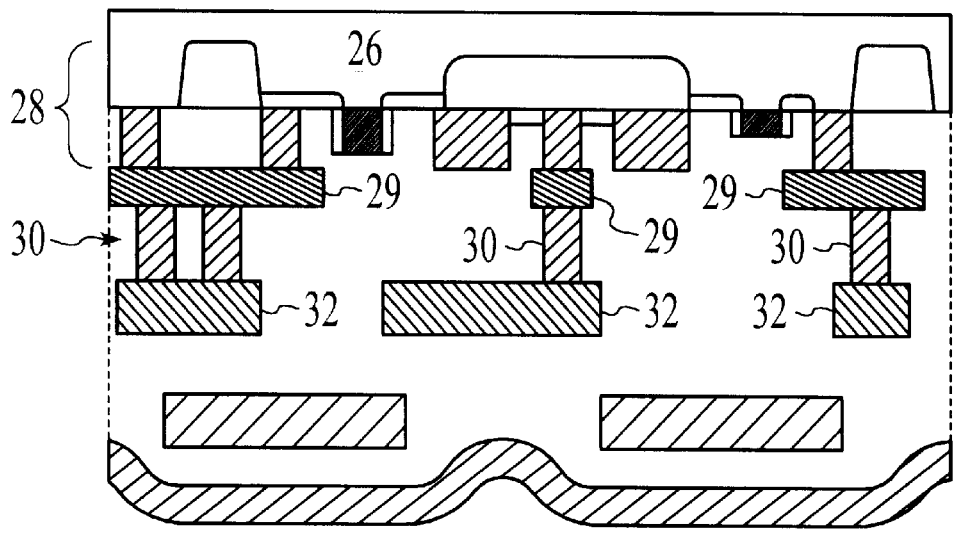
FIG. 4 illustrates a partial cross-section of the flip-chip device of FIG. 3 following reduction of a backside layer.
Figure 5:
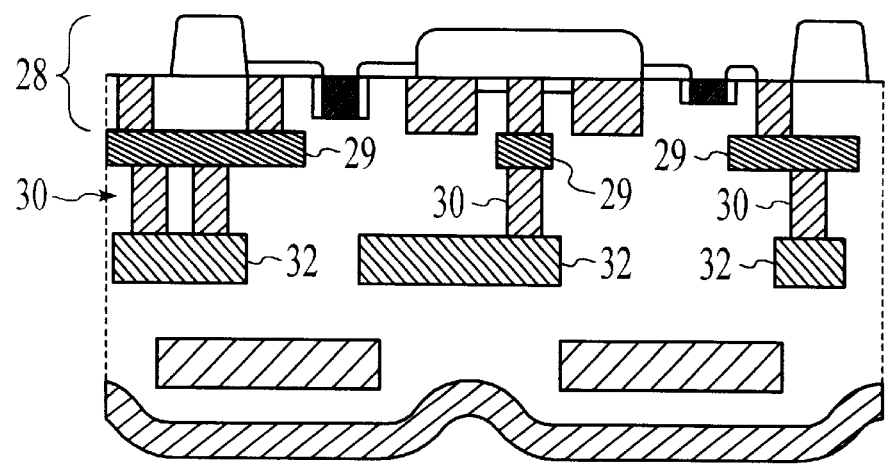
FIG. 5 illustrates a partial cross-section of the flip-chip device of FIG. 3 following exposure of an active region.

FIG. 3 illustrates a partial cross-section of a flip-chip device prior to the deprocessing of FIG. 2. As shown in FIG. 3, a first layer encountered from the backside is the reduced silicon layer 26, followed by an active transistor region 28. The deprocessing initiates with reduction of the first backside layer to a predetermined thickness (step 18, FIG. 2). In a preferred embodiment, the reduction utilizes mechanical polishing to remove the backside layer, i.e., silicon, until a desired thickness is reached. Suitably, the thickness of the silicon is reduced from about 100 $\mu$m to about 10 $\mu$m. Alternatively, reactive ion etching (RIE) for silicon could be used in place of the mechanical polishing to reduce the thickness of the silicon layer. FIG. 4 illustrates a partial cross-section of the flip-chip device of FIG. 3 following step 18. Once the desired thickness is reached, exposure of the active transistor region 28 suitably occurs (step 19, FIG. 2), preferably using RIE, since RIE is considered more controllable than mechanical polishing for removing a remaining amount of silicon. FIG. 5 illustrates a partial cross-section of the flip-chip device having active region 28 exposed.

With the active region exposed, a determination of whether an actual defect has been found occurs (step 20, FIG. 2), e.g., through the use of a standard SEM (scanning electron microscope) system for defect inspection. If a defect is found, the deprocessing is completed. If a defect is not found, deprocessing continues with device analysis (step 21, FIG. 2), e.g., an optical and SEM inspection of the device, as is well understood by those skilled in the art. A metal layer is then removed (step 22, FIG. 2), as represented by the removal of layer 29 in the partial cross-section of the flip-chip device shown in FIG. 6. Mechanical polishing is suitable for removing the metal layer and thick ILD layer, while RIE is suitable for removing the dielectric materials in the active region and to expose the metal layer for inspection before metal layer removal.

Figure 6:
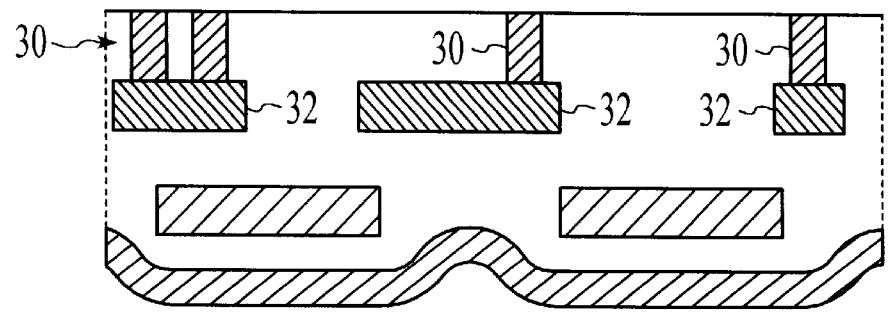
FIG. 6 illustrates a partial cross-section of the flip-chip device of FIG. 3 following removal of a metal layer.
Figure 7:
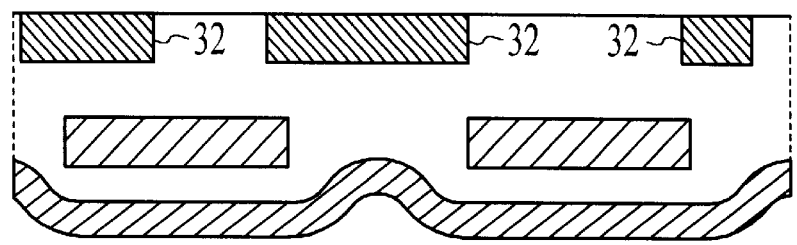
FIG. 7 illustrates a partial cross-section of the flip-chip device of FIG. 3 following removal of ILD material.

Removal of the metal layer exposes a layer of interlayer dielectric (ILD) material 30, e.g., silicon dioxide ($SiO_2$), as shown in the partial cross-section of FIG. 6. Deprocessing thus continues with removal of the ILD layer 30 (step 23, FIG. 2). Preferably, the ILD layer 30 is polished off substantially close to a next metal layer followed with RIE to etch remaining ILD material off of the next metal layer. As shown by the partial cross-section of FIG. 7, removal of ILD layer 30 via the etching step 23 exposes a next metal layer 32.

Since more layers exist beneath layer 30, delayering is not complete, as determined via step 24, FIG. 2, and deprocessing continues from step 21 for the exposed metal layer 32. Thus, the deprocessing proceeds as described above for each exposed metal layer and ILD layer until delayering and device analysis are completed.

Although the present invention has been described in accordance with the embodiments shown, one of ordinary skill in the art will recognize that there could be variations to the embodiment and those variations would be within the spirit and scope of the present invention. For example, although the present invention has been described in terms of silicon based ICs, flip-chip ICs formed with other substrates may be processed using suitable processing conditions for those substrates in accordance with the deprocessing methods described herein. Accordingly, many modifications may be made by one of ordinary skill without departing from the spirit and scope of the present invention, the scope of which is defined by the following claims.

What is claimed is:

1. A method for device deprocessing from a backside of a multi-layer integrated circuit utilized in a flip-chop orientation, the method comprising:
   a) reducing a first backside layer of the multi-layer integrated circuit to a predetermined thickness;
   b) exposing an active region utilizing reactive ion etching of the multi-layer integrated circuit to allow device analysis of the multi-layer integrated circuit;
   c) removing a metal layer utilizing mechanical polishing beneath the active region to expose interlayer dielectric material;
   d) performing a bulk delayering utilizing reactive ion etching of the interlayer dielectric material to expose a next metal layer; and
   e) continuing to perform steps c) and d) until device analysis and delayering from the backside is completed, wherein the device is inspected to determine if there is a defect after steps c) and d).

2. The method of claim 1 wherein reducing step (a) further comprises mechanically polishing the first backside layer to the predetermined thickness.

3. The method of claim 1 wherein reducing step (a) further comprises performing reactive ion etching to reach the predetermined thickness.

4. The method of claim 1 wherein the first backside layer comprises a silicon layer.

5. The method of claim 1 wherein the predetermined thickness comprises a thickness of about 10 $\mu$m.

6. A method for deprocessing a flip-chip multi-layer integrated circuit from a backside, the method comprising:
   a) detecting a location of a defect in the multi-layer integrated circuit;
   b) reducing a substrate layer of the multi-layer integrated circuit to a predetermined thickness;
   c) exposing an active region utilizing reactive ion etching in the multi-layer integrated circuit to allow analysis of the active region;
   d) inspecting a metal layer beneath the active region when the analysis does not find a defect;
   e) removing the metal layer utilizing mechanical polishing to expose a layer of interlayer dielectric material;
   f) etching the interlayer dielectric material utilizing reactive ion etching to expose a next metal layer; and
   g) continuing to perform steps d), e), and f) until device analysis and delayering from the backside are complete.

7. The method of claim 6 wherein detecting step (a) further comprises removing a bulk portion of substrate material, and performing device diagnostic until a defect is located.

8. The method of claim 6 wherein the reducing step (b) further comprises mechanically polishing the substrate layer from a thickness of about 100 $\mu$m to about 10 $\mu$m.

9. The method of claim 6 wherein etching the interlayer dielectric material further comprises performing reactive ion etching of silicon dioxide.

* * * * *